United States Patent [19]

Larson

[11] Patent Number: 4,556,562

[45] Date of Patent: Dec. 3, 1985

[54] STABLE ANTI-PEST NEEM SEED EXTRACT

[75] Inventor: Robert O. Larson, Sheboygan, Wis.

[73] Assignee: Vikwood, Ltd., Sheboygan, Wis.

[21] Appl. No.: 590,808

[22] Filed: Mar. 19, 1984

[51] Int. Cl.⁴ ...................... A01N 65/00; A01N 43/16
[52] U.S. Cl. .................................. 424/195.1; 514/453
[58] Field of Search ..................... 424/195, 279, 195.1, 424/453

[56] References Cited

U.S. PATENT DOCUMENTS 963,932 7/1910 Olsson ................................. 424/127
3,663,253 5/1972 Stone .................................. 106/204

OTHER PUBLICATIONS

Radwanski, S. A., et al., "Vegetative Fallows and Potential Value of the Neem Tree (*Azadirachta indica*) in the Tropics", *Economic Botony*, 35(4), 398–414 (1981).
Stokes, J. B. et al., "Effect of Sunlight on Azadirachtin: Antifeeding Potency", *J. Environ. Sci. Health*, A17(1), 57–65 (1982).
Uebel, E. C., et al., "Preparative Reversed-Phase Liquid Chromatographic Isolation of Azadirachtin from Neem Kernels", *J. of Liquid Chromatography*, 2(6) 875–882 (1979).
Warthen, J. D. et al. Journal of Liquid Chromatography, 7(3), 591–598.

*Primary Examiner*—Allen J. Robinson
*Assistant Examiner*—John W. Rollins

[57] ABSTRACT

Storage stable composition effective as a biorational agent for protection against pests, e.g. Japanese beetles, is a diluted ethanol neem seed extract comprising from about 2,000 to about 4,000 ppm azadirachtin and having a pH ranging from about 3.5 to about 6.0.

18 Claims, No Drawings

STABLE ANTI-PEST NEEM SEED EXTRACT

TECHNICAL FIELD

This invention relates to a composition for protecting food and fiber crops from harmful pests, and also to a process for preparing the same.

BACKGROUND OF THE INVENTION

For many years now, several powerful and effective insecticides have been used to protect food and fiber crops. More recently, there has been a great deal of controversy about the effect of these on the environment and some of the insecticides which have been in common use have been banned. Furthermore, other insecticides which are still in use are considered to be potentially harmful to the environment but are required to be used for lack of other alternatives.

As a result, a search has been going on for "biorational pesticides". These are compositions which would deter insects or other pests but would have no or minimal harmful effect on the environment.

One agent known to protect crops from pests is azadirachtin which is a natural product found in the seeds of the neem tree (*Azadirachta indica* A. Juss.). The neem tree is found in India, Pakistan, Bangladesh, Burma, Thailand, Malaysia and Africa, for example.

Azadirachtin has been extracted from neem seeds and found to have anti-feedant (deters insects from feeding on plants) and growth regulation potency against several pests including Japanese beetles, fall armyworms, locusts, termites, grasshoppers, tobacco hornworms, tobacco budworms, caterpillars, gypsy moths, rice weevils, aphids, cotton boll moths, and many others. It is readily applied by coating seeds or by applying a spray to the crops themselves. See for example J. Environ. Sci. Health, A17 (1), 57–65 (1982) by J. B. Stokes and R. E. Redfern of the USDA.

While azadirachtin is a known agent, it has not come into commercial use because it has stability problems. For example, its instability in sunlight has been known and is the subject of the aforementioned article by Stokes and Redfern. That article indicates that sunlight degradation is hindered by leaving some neem oil in with the azadirachtin or by adding other plant oil and that further aid is given by including a sunscreen (a uv-absorbing additive). Azadirachtin has also been found to have storage stability problems whereby it deactivates in the container or after application simply on the passage of time. No solution has been suggested in the published literature for these problems.

SUMMARY OF THE INVENTION

It has now been discovered that a storage stable composition containing azadirachtin comprises from about 2,000 to about 4,000 ppm azadirachtin and has a pH ranging from about 3.5 to about 6.0. By storage stable is meant retaining more than about 80% of its potency when in the form of an emulsion 8 weeks or more after formation of the emulsion and more than 50% of its potency even after two years.

The composition, in the preferred embodiment, is a diluted ethanol extract of neem seeds wherein the pH has been adjusted to the aforestated level. This composition besides being storage stable, has the advantage of being economical to prepare. It is suitable for use as a biorational agent for protection against pests.

Preferably, the composition comprises from about 20% to about 25% neem oil. Neem oil is the triglyceride constituent normally found in the neem seeds. As indicated in the aforementioned article, it has an effect on protecting the azadirachtin from sunlight degradation. It is readily extracted from the neem seeds at the same time as the azadirachtin.

A process herein comprises the steps of
(a) forming neem seed particles;
(b) extracting the particles with extraction agent comprising ethanol at a temperature ranging from about 60° C. to about 90° C. and separating the extract to obtain a solution comprising from about 5,000 to about 10,000 ppm azadirachtin;
(c) diluting to form an emulsion comprising from about 2,000 to about 4,000 ppm azadirachtin;
(d) measuring the pH, and if it is outside the range of from about 3.5 to about 6.0, adjusting the pH to range from about 3.5 to about 6.0.

All percentages and parts herein are by weight unless otherwise stated.

DETAILED DESCRIPTION

The composition herein preferably contains azadirachtin at a level ranging from about 2,500 to about 3,500 and has a pH ranging from about 3.8 to about 4.2. Optimally, it contains azadirachtin at a level of about 3,000 ppm and has a pH ranging from about 3.84 to about 4.0.

It has been found that the concentration of azadirachtin and pH level are both very important in respect to storage stability and that inside the limits recited herein azadirachtin levels are substantially maintained up to eight weeks or more (with up to 65% potency being retained even after two years); whereas outside the ranges herein, azadirachtin levels are reduced for example in a shorter period of time for example in about three weeks or even less.

As previously indicated, it is highly desirable to retain at least some of the neem oil present in the neem seeds in the composition herein. It is noted that the amount of neem oil present in neem seeds varies substantially from batch to batch and according to the literature comprises from about 20% to about 50% of neem seeds.

It is highly preferred to include an emulsifying agent in the composition so that the azadirachtin and neem oil and any other ingredients are kept uniformly distributed in the composition. The percentage of the composition which is emulsifier normally depends on the emulsifier which is used. Typically, the emulsifying agent (that is the active ingredient) is used in an amount ranging from about 0.2% to about 30% of the composition and often is used at a level of from about 15% to about 25%.

Preferred emulsifying agents are those normally utilized in foods and include sorbitan esters, ethoxylated and propoxylated mono- or diglycerides, acetylated mono- or diglycerides, lactylated mono- or diglycerides, citric acid esters of mono- or diglycerides, sugar esters, polysorbates and polyglycerol esters. Preferred emulsifier is polyoxyethylene sorbitan monolaurate which is sold under the name Tween 20 ®.

It is preferred to include as an optional ingredient a sunscreen at a level, for example, of about 1% to about 2.5%. A preferred sunscreen is p-aminobenzoic acid or its esters.

We turn now to the process herein for economically making a preferred storage stable composition herein.

The step of forming neem seed particles involves comminuting or otherwise size-reducing, typically to form particles ranging in size from about 350 microns to about 2 millimeters (maximum dimension). A very preferred size is that of the size of a regular grind of coffee. According to the U.S. Department of Commerce (see Coffee Brewing Workshop Manual, p. 33, published by the Coffee Brewing Center of the Pan American Coffee Bureau), regular grind has a particle size defined by 33% retained on 14 mesh Tyler standard sieve, 55% retained on a 28 mesh Tyler standard sieve and 12% passing through a 28 mesh Tyler standard sieve. The comminuting or size-reduction is readily carried out on standard apparatus for this purpose, for example a standard commercial feed mill or a coffee mill such as an American Duplex Model 480 grinder.

The "regular grind" is preferred because extraction is easily carried out on this particle size. The avoidance of a high percentage, for example 30% or more, of fine particles is preferred because the inclusion of such a large percentage of fine particles will require extraction by special means and hinder separation of the extract from the particles.

If desired, the particles may be compressed, for example, using a roll mill to disrupt cellular structure for easier extraction.

The extraction is preferably carried out using ethanol at a temperature ranging from about 75° C. to about 85° C. and optimally at 80° C. Very preferably, extraction is carried out to obtain a solution comprising about 10,000 ppm azadirachtin which is the solubility limit for azadirachtin in ethanol. Very preferably extraction is carried out to obtain a solution containing from about 40% to about 45% neem oil.

The extraction is readily carried out by passing a batch of the extracting agent which has been heated to the aforementioned temperature through the particles of neem seeds. The separation of the extract from the particles is readily carried out for example using vacuum filtration or centrifugation or other common separating method.

The extraction is preferably carried out by a process involving multiple passes of the extracting agent through the particles. This involves, for example, passing a batch of extracting agent through the particles and recovering it and then passing the same batch of extracting agent through the particles again and continuing this process until a total of 8 to 12, preferably 10, passes of the extracting agent have been made through the particles, with the extracting agent being heated to the aforementioned temperatures between passes if necessary.

The step of diluting to form an emulsion comprises adding diluent, preferably water, and emulsifying agent to obtain an emulsion comprising from about 2,000 to about 4,000 ppm azadirachtin and usually from about 20% to about 25% neem oil. Where the emulsifying agent is obtained commercially in very diluted form, this diluting step is carried out simply by admixing the emulsifying agent as purchased with the extract. Preferably the emulsifying composition contains water in addition to the emulsifying agent and the water forms at least the main portion of the diluent. The diluting step, of course, should be carried out prior to any substantial degradation of the azadirachtin potency.

The pH of the resulting diluted extract varies from batch to batch of neem seed starting material. In a very few instances, the pH may already be within the required limits. However, usually pH adjustment is required. Even if pH measurement indicates a pH within the aforestated limits, optimization may be desired. The pH adjustment is carried out by the addition preferably of a base which is not toxic or harmful to the environment in the concentration utilized. The preferred agent is ammonium hydroxide as the ammonium constituent is nutritious to the plants to which the composition is applied. Other pH adjustment agents include, for example, sodium or potassium hydroxide.

The sunscreen is preferably added after pH adjustment but it can be admixed before this.

Preferred embodiments of the invention herein are illustrated in the following specific examples.

EXAMPLE I 40 lbs. of neem seeds imported from India is ground using a standard commercial feed mill to the size of a regular grind of coffee.

250 grams of the grind is positioned in a columnar extraction system and 250 ml. of ethanol at 80° C. is passed through the grind using vacuum filtration to recover the extract. The product is heated up to 80° C. again and is passed through the grind again. This is repeated for 10 cycles, i.e. the ethanol is passed through the grind a total of 10 times with the concentration of extracted matter increasing each time. At the end of the 10 cycles, the extract contained 10,000 ppm azadirachtin and 40% neem oil. About 90% of the available azadirachtin is recovered from the seeds. Some ethanol flashes off during the processing.

To the extract is added Tween 20 ® (consisting of water and polyoxyethylene sorbitan monolaurate) to obtain a diluted extract containing 3,000 ppm azadirachtin and 20% neem oil.

To the resulting emulsion is added ammonium hydroxide to adjust the pH to 4.0.

The resulting product is an effective biorational agent against a wide spectrum of pests and is shelf stable for more than 8 weeks after formulation.

Product containing 3,000 ppm azadirachtin and having a pH of 4.0 maintained under normal shelf life conditions (without refrigeration or addition of sunscreen) was found to have retained 65% of its potency even two years later.

EXAMPLE II

Processing is carried out as in Example I except that the emulsifying agent is Triton X-100 (0.5 parts to one part concentrated extract) and neutralization is carried out to pH's as listed below. Triton X-100 is an octyl phenoxy polyethoxy ethanol.

Azadirachtin levels (ppm) on storage were measured with the following results:

| Azadirachtin Levels (ppm) on Storage at Several pH Values Storage Time (weeks) | | | | | |
|---|---|---|---|---|---|
| pH | 0 | 1 | 2 | 3 | 8 |
| 3.84 | 3138 | 2841 | 3214 | 2500 | 3200 |
| 4.80 | 3047 | 3105 | 2680 | 2460 | 2900 |
| 5.99 | 2473 | 2847 | 3143 | 2260 | 2370 |
| 6.77 | 2644 | 2408 | 2877 | 2180 | — |
| 7.90 | 2690 | 2010 | 1431 | 1520 | — |

As can be seen from the above tables, solubility of azadirachtin is reduced as pH is raised and there is a storage stability advantage at lowest three pH's.

EXAMPLE III

Processing is carried out as in Example I except that extraction and separation of extract from neem seed particles is carried out by centrifuging. The resulting product is effective against a wide spectrum of pests.

REFERENCE EXAMPLE I

Product containing 10,000 ppm azadirachtin and having a pH less than 3.5 was found to have its azadirachtin concentration reduced to 2,500 ppm within approximately one month.

While the foregoing describes preferred embodiments, modifications within the scope of the invention will be evident to those skilled in the art.

For example, some of the ethanol in the extracting agent, e.g. 20% by volume, can be replaced with water.

Thus, the scope of the invention is intended to be defined by the claims.

What is claimed is:

1. A process for preparing a storage stable neem seed extract, said process comprising the steps of:
    (a) forming neem seed particles ranging in size from about 350 microns to about 2 millimeters (maximum dimension);
    (b) extracting the paticles with extracting agent comprising ethanol at a temperature ranging from about 60° C. to about 90° C. and separating the extract to obtain a solution comprising from about 5,000 to about 10,000 ppm azadirachtin;
    (c) diluting to form an aqueous emulsion comprising from about 2,000 to about 4,000 ppm azadirachtin;
    (d) measuring the pH, and if it is outside the range of from about 3.5 to about 6.0, adjusting the pH to range from about 3.5 to about 6.0.

2. Process as recited in claim 1 wherein in step (b), the solution obtained contains from about 40 to about 45% neem oil.

3. Process as recited in claim 2, wherein extracting is carried out by passing a batch of extracting agent through the particles 8 to 12 times and wherein the extracting agent is utilized at a temperature ranging from about 75° C. to about 85° C.

4. Process as recited in claim 3, wherein diluting to form an emulsion is carried out by using water in combination with nonionic emulsifying agent.

5. Process as recited in claim 4, wherein the extracting is carried out utilizing extracting agent at about 80° C. and passing such through the particles 10 times to obtain a solution comprising about 10,000 ppm azadirachtin, and wherein diluting is carried out to form an emulsion comprising about 3,000 ppm azadirachtin and wherein the pH is adjusted to about 4.

6. Process as recited in claim 5, wherein the pH adjustment is carried out by addition of ammonium hydroxide.

7. Process as recited in claim 6, wherein separation of extract from the particles is carried out utilizing vacuum filtration.

8. Process as recited in claim 6, wherein separation of extract from the particles is carried utilizing centrifugation.

9. Process as recited in claim 6, wherein sunscreen comprising p-aminobenzoic acid or its esters is added to be present at a level ranging from about 1% to about 2.5%.

10. Process as recited in claim 1, wherein the diluting is carried out to form an emulsion comprising from about 2,500 to about 3,500 and the pH is adjusted to be from about 3.8 to about 4.2.

11. Process as recited in claim 10, wherein diluting is carried out to form an emulsion comprising about 3,000 ppm azadirachtin.

12. A storage stable aqueous azadirachtin-containing composition, said composition comprising from about 2,000 to about 4,000 ppm azadirachtin, said composition having a pH ranging from about 3.5 to about 6.0.

13. A storage stable composition as recited in claim 12 comprising from about 20% to about 25% neem oil.

14. A storage stable composition as recited in claim 13 which is derived from an ethanol extract of neem seeds.

15. A storage stable composition as recited in claim 14 which comprises from about 2,500 to about 3,500 ppm azadirachtin and has a pH ranging from about 3.8 to about 4.2.

16. A storage stable composition as recited in claim 12, wherein the azadirachtin is present at a level of about 3,000 ppm.

17. A storage stable composition as recited in claim 16 which contains from about 15% to about 25% nonionic emulsifying agent.

18. A storage stable composition as recited in claim 17, comprising additionally from about 1% to about 2.5% sunscreen comprising p-aminobenzoic acid or its esters.

* * * * *

UNITED STATES PATENT AND TRADEMARK OFFICE
CERTIFICATE OF CORRECTION

PATENT NO. : 4,556,562

DATED : December 3, 1985

INVENTOR(S) : Robert O. Larson

It is certified that error appears in the above—identified patent and that said Letters Patent is hereby corrected as shown below:

In the list of OTHER PUBLICATIONS on the cover page, additionally include the following Recent Advances in Phytochemistry, Chapter 11, by Koji Nakanishi, 1979, pp 283, 288, 289

Chemical Abstracts 102:41598u, 1985, "Isolation from Neem Oil of Active Principles Evincing Oviposition Deterrent Activity in Insects"

Claim 10, line 3, after "3,500" insert --ppm azadiractin--.

Claim 16, line 2, "12" should be --15--.

Signed and Sealed this

Twenty-fifth Day of March 1986

[SEAL]

Attest:

DONALD J. QUIGG

Attesting Officer

Commissioner of Patents and Trademarks